(12) United States Patent
Song et al.

(10) Patent No.: US 8,476,230 B2
(45) Date of Patent: Jul. 2, 2013

(54) INSULINOTROPIC COMPLEX USING AN IMMUNOGLOBULIN FRAGMENT

(75) Inventors: Dae Hae Song, Seoul (KR); Chang Ki Lim, Suwon-si (KR); Tae Hun Song, Yongin-si (KR); Young Hoon Kim, Seoul (KR); Se Chang Kwon, Seoul (KR); Gwan Sun Lee, Seoul (KR); Sung Youb Jung, Suwon-si (KR); In Young Choi, Yongin-si (KR)

(73) Assignee: Hanmi Science Co., Ltd, Hwaseong-si (KR)

(*) Notice: Subject to any disclaimer, the term of this patent is extended or adjusted under 35 U.S.C. 154(b) by 119 days.

(21) Appl. No.: 12/523,050

(22) PCT Filed: Jan. 4, 2008

(86) PCT No.: PCT/KR2008/000061
§ 371 (c)(1),
(2), (4) Date: Feb. 2, 2010

(87) PCT Pub. No.: WO2008/082274
PCT Pub. Date: Jul. 10, 2008

(65) Prior Publication Data
US 2010/0105877 A1 Apr. 29, 2010

(30) Foreign Application Priority Data
Jan. 5, 2007 (KR) .................... 10-2007-0001662

(51) Int. Cl.
*A61K 38/00* (2006.01)
*A61K 39/395* (2006.01)
*A61P 5/50* (2006.01)

(52) U.S. Cl.
USPC ............... 514/6.9; 514/6.7; 514/6.8; 514/7.2; 514/11.7; 424/195.11

(58) Field of Classification Search
None
See application file for complete search history.

(56) References Cited

U.S. PATENT DOCUMENTS

| | | | |
|---|---|---|---|
| 5,424,686 A | 6/1995 | Wong et al. | |
| 5,545,618 A | 8/1996 | Buckley et al. | |
| 6,756,480 B2 | 6/2004 | Kostenuik et al. | |
| 6,924,264 B1 | 8/2005 | Prickett et al. | |
| 7,157,555 B1 | 1/2007 | Beeley et al. | |
| 2006/0019347 A1* | 1/2006 | Cho et al. | ..................... 435/69.1 |

FOREIGN PATENT DOCUMENTS

| | | |
|---|---|---|
| CN | 1723220 A | 1/2006 |
| EP | 0 733 644 A1 | 9/1996 |
| KR | 10-2004-0038901 A | 5/2004 |
| KR | 10-2005-0047031 A | 5/2005 |
| KR | 10-2006-0106486 A | 10/2006 |
| KR | 10-2006-0109940 A | 10/2006 |
| WO | 96/32478 A1 | 10/1996 |
| WO | 97/34631 A1 | 9/1997 |
| WO | WO 02/46227 * | 11/2001 |
| WO | WO 02/46227 A2 | 6/2002 |
| WO | WO 02/066514 A2 | 8/2002 |
| WO | 2004/056317 A2 | 7/2004 |
| WO | 2004/093823 A2 | 11/2004 |
| WO | 2005/000892 A2 | 1/2005 |
| WO | 2005/047334 A1 | 5/2005 |
| WO | 2006/068910 A1 | 6/2006 |
| WO | 2006/076471 A2 | 7/2006 |
| WO | 2006/107124 A1 | 10/2006 |
| WO | 2006/124529 A1 | 11/2006 |

OTHER PUBLICATIONS

European Search Report issued in corresponding EP Application No. 08 70 4601, dated Jul. 2010.
International Search Report issued in corresponding PCT Application No. PCT/KR2008/000061, dated Apr. 28, 2008.
Korean Patent Office, Korean Notice of Allowance issued in KR Application No. 10-2007-0001662, dated Aug. 1, 2011.
Parkes et al., "Insulinotropic actions of exendin-4 and glucagon-like peptide-1 in vive and in vitro," Metabolism, 2001, vol. 50, No. 5, Abstract.
Russian Patent Office, Russian Office Action issued in RU Application No. 2009129953/15, dated Oct. 13, 2010.
Singaporean Patent Office, Singaporean Office Action issued in SG Application No. 200904297-9, dated Nov. 12, 2010.
Chinese Patent Office, Chinese Office Action issued in corresponding CN Application No. 200880001766.4, dated Sep. 22, 2011.
Japanese Patent Office, Japanese Office Action issued in corresponding JP Application No. 2009-544800, dated Sep. 25, 2012.
Chinese Patent Office, Chinese Office Action issued in corresponding CN Application No. 200880001766.4, dated Feb. 17, 2013.

* cited by examiner

*Primary Examiner* — Robert Landsman
*Assistant Examiner* — Ian Dang
(74) *Attorney, Agent, or Firm* — Sughrue Mion, PLLC

(57) ABSTRACT

The present invention relates to an insulinotropic peptide conjugate having improved in-vivo duration of efficacy and stability, comprising an insulinotropic peptide, a non-peptide polymer and an immunoglobulin Fc region, which are covalently linked to each other, and a use of the same. The insulinotropic peptide conjugate of the present invention has the in-vivo activity which is maintained relatively high, and has remarkably increased blood half-life, and thus it can be desirably employed in the development of long acting formulations of various peptide drugs.

20 Claims, 6 Drawing Sheets

1: Non-reduction condition
2: Reduction condition

Fig. 14

INSULINOTROPIC COMPLEX USING AN IMMUNOGLOBULIN FRAGMENT

This is a national stage application of PCT/KR2008/000061 filed on Jan. 4, 2008, which claims priority from Korean patent application 10-2007-0001662 filed Jan. 5, 2007, contents of which are incorporated herein by reference.

TECHNICAL FIELD

The present invention relates to an insulinotropic peptide conjugate for long acting formulation of an insulinotropic peptide. Specifically, the present invention relates to a modified insulinotropic peptide conjugate having a remarkably improved in-vivo duration of efficacy generated by covalently linking the insulinotropic peptide with a non-peptidyl polymer and an immunoglobulin Fc, and a method for preparation thereof.

BACKGROUND ART

Peptides tend to be easily denatured due to their low stability, degraded by in-vivo proteolytic enzymes, thus losing the activity, and have a relatively small size, thereby easily passing through the kidney. Accordingly, in order to maintain the blood levels and the titers of a medicament comprising a peptide as a pharmaceutically effective component, it is necessary to administer the peptide drug frequently to a patient to maintain desired blood levels and titers. However, the peptide drugs are usually administered in the form of injectable preparations, and such frequent administration cause severe pain for the patients. To solve these problems, many efforts have been made. As one of such efforts, there has been an attempt to transfer the peptide drug through oropharyngeal or nasopharyngeal inhalation by increasing the transmission of the peptide drug through the biological membranes. However, this approach is still difficult in maintaining the in-vivo activity of the peptide drug due to the low in-vivo transfer efficiency, as compared to the injection.

On the other hand, many efforts have been made to improve the blood stability of the peptide drug, and to maintain the drug in the blood at a high level for a prolonged period of time, thereby maximizing the pharmaceutical efficacy of the drug. The long acting preparation of such peptide drug therefore needs to increase the stability of the peptide drug, and to maintain the titers at sufficiently high levels without causing immune responses in patients.

As a method for stabilizing the peptide, and inhibiting the degradation by a proteolytic enzyme, some trials have been performed to modify a specific amino acid sequence which is sensitive to the proteolytic enzyme. For example, GLP-1 (7-37 or 7-36 amide), which functions to reduce the glucose concentration in blood for treating a Type 2 diabetes, has a short half-life of the physiological activity of about 4 minutes or less (Kreymann et al., 1987), due to loss of the titers of GLP-1 through the cleavage between the 8th amino acid (Ala) and the 9th amino acid (Asp) by a dipeptidyl peptidase IV (DPP IV). As a result, various investigations have been made on a GLP-1 analog having resistance to DPP IV, and trials have been made for substitution of Ala$^8$ with Gly (Deacon et al., 1998; Burcelin et al., 1999), or with Leu or D-Ala (Xiao et al., 2001), thereby increasing the resistance to DPP IV, while maintaining the activity. The N-terminal amino acid, His$^7$ of GLP-1 is critical for the GLP-1 activity, and serves as a target of DPP IV. Accordingly, U.S. Pat. No. 5,545,618 describes that the N-terminus is modified with an alkyl or acyl group, and Gallwitz, et al. describes that 7th His was subject to N-methylation, or alpha-methylation, or the entire His is substituted with imidazole to increase the resistance to DPP IV, and to maintain physiological activity.

In addition to these modifications, an exendin-4, which is a GLP-1 analog purified from the salivary gland of a glia monster (U.S. Pat. No. 5,424,686), has resistance to DPP IV, and higher physiological activity than GLP-1. As a result, it had an in-vivo half-life of 2 to 4 hours, which was longer than that of GLP-1. However, with the method for increasing the resistance to DPP IV only, the physiological activity is not sufficiently sustained, and for example, in the case of a commercially available exendin-4 (exenatide), it needs to be injected to a patient twice a day, which is still difficult for patients.

These insulinotropic peptides have a problem, usually in that the size of the peptide is small. Thus, they cannot be recovered in the kidney, and are then extracorporeally discharged. Accordingly, a method for chemically adding a polymeric substance having high solubility, such as polyethylene glycol (PEG), onto the surface of the peptide to inhibit the loss in the kidney, has been used.

PEG non-specifically binds to a specific site or various sites of a target peptide to give an effect of increasing the molecular weight of a peptide, and thus inhibiting the loss by the kidney, and preventing hydrolysis, without causing any side-effects. For example, International Pat. Publication No. WO 2006/076471 describes that PEG binds to a B-type natriuretic peptide, or BNP, which binds to NPR-A to activate the production of cGMP, which leads to reduction in the arterial blood pressure, and as a result, is used as congestive heart failure therapeutic agent, thereby sustaining the physiological activity. U.S. Pat. No. 6,924,264 describes that PEG binds to the lysine residue of an exendin-4 to increase its in-vivo residence time. However, this method increases the molecular weight of PEG, thereby increasing the in-vivo residence time of the peptide drug, while as the molecular weight is increased, the titer of the peptide drug is remarkably reduced, and the reactivity with the peptide is also reduced. Accordingly, it undesirably lowers the yield.

International Pat. Publication No. WO 02/46227 describes a fusion protein prepared by coupling GLP-1, an exendin-4, or an analog thereof with human serum albumin or an immunoglobulin region (Fc) using a genetic recombination technology. U.S. Pat. No. 6,756,480 describes an Fc fusion protein prepared by coupling a parathyroid hormone (PTH) and an analog thereof with Fc region. These methods can address the problems such as low pegylation yield and non-specificity, but they still have a problem in that the effect of increasing the blood half-life is not noticeable as expected, and sometimes the titers are also low. In order to maximize the effect of increasing the blood half-life, various kinds of peptide linkers are used, but an immune response may be possibly caused. Further, if a peptide having disulfide bonds, such as BNP is used, there is a high probability of misfolding. As a result, such peptide can hardly be used.

In addition, a GLP-1 derivative, NN2211, is prepared by substitution of the amino acid of GLP-1, and is bound to an acyl side chain to form a non-covalent bond with albumin, thereby increasing its in-vivo residence time. However, it has a half-life of 11 to 15 hours, which does not indicate remarkable increase in the half-lives, as compared with the exendin-4. Thus, the GLP-1 derivative still needs to be injected once a day (Nauck et al., 2004). Further, CJC-1131 is a GLP-1 derivative having a maleimide reactive group for covalently binding the GLP-1 with albumin in blood, and efforts had been tried to develop the CJC-1131 for the purpose of increasing the in-vivo half-life, but such efforts were now stopped. A subsequently suggested substance, CJC-1134, is an exendin-4 which covalently binds to a recombinant albumin, and did not exhibit a remarkable effect of increasing blood stability, with the blood half-life being about 17 hours (Rat) (Thibauoleau et. al., 2006).

DISCLOSURE

Technical Problem

Thus, the present inventors linked an immunoglobulin Fc, and a non-peptidyl polymer, to an insulinotropic peptide site-specifically at an amino acid residue other than the N-terminus by a covalent bond, and found that the conjugate of the present invention exerts a remarkably increased in-vivo efficacy and half life. Especially, they have found that, among the insulinotropic peptide conjugates, the conjugates of the peptides such as Exendin-4, des-amino-histidyl exendin-4 where the N-terminal amine group of exendin-4 is deleted, beta-hydroxy-imidazo-propionyl exendin-4 where the N-terminal amine group of exendin-4 is substituted with hydroxyl group, dimethyl-histidyl exendin-4 where the N-terminal amine group of exendin-4 is modified with two methyl groups, and an imidazo-acetyl-exendin-4 where the alpha carbon of the first histidine and the N-terminal amine group liked thereto are deleted, exert a remarkably increased in-vivo efficacy and half life.

Technical Solution

It is an object of the present invention to provide a long acting preparation of insulinotropic peptide, having the effects of maintaining the in-vivo activity of the insulinotropic peptide and increasing the blood half-life.

BRIEF DESCRIPTION OF DRAWINGS

In FIG. 14, HM11260A is exendin-4 (Lys27)-PET-Fc; HM11260D is DA exendin-4 (Lys27)-PET-Fc; HM11260DM is DM exendin-4 (Lys27)-PET-Fc; HM11260S is Ser12 DA exendin-4 (Lys27)-PET-Fc; HM11260C is CA exendin-4 (Lys27)-PET-Fc; and HM11260H is HY exendin-4 (Lys27)-PET-Fc.

DETAILED DESCRIPTION

In one embodiment of the present invention, there is provided a long acting insulinotropic peptide conjugate, in which an insulinotropic peptide and a non-peptidyl polymer possessing a reactive group at both ends thereof are covalently linked to each other.

The insulinotropic peptide of the present invention is a peptide possessing an insulinotropic function for promoting the synthesis and the expression of insulin in a pancreatic beta cell. These peptides include a precursor, an agonist, a derivative, a fragment, and a variant, and preferably GLP (glucagon like peptide)-1, exendin 3, and exendin 4.

GLP-1 is a hormone that is secreted by the small intestine, generally promotes the biosynthesis and secretion of insulin, inhibits the secretion of glucagon, and promotes glucose absorption in the cells. In the small intestine, a glucagon precursor is decomposed into three peptides, that is, glucagon, GLP-1, and GLP-2. Here, the GLP-1 means GLP-1 (1-37), which is originally in the form having no insulinotropic function. But it is then processed and converted into one in the activated GLP-1 (7-37) form. The sequence of the GLP-1 (7-37) amino acid is as follows:

GLP-1(7-37)

(SEQ ID NO: 1)
HAEGT FTSDV SSYLE GQAAK EFIAW LVKGR G

The GLP-1 derivative means a peptide which exhibits an amino acid sequence homology of at least 80% with that of GLP-1, may be in the chemically modified form, and exhibits an insulinotropic function of at least equivalent or more to that of GLP-1.

The GLP-1 fragment means one in the form in which one or more amino acids are added or deleted at an N-terminus or a C-terminus of a native GLP-1, wherein the added amino acid is possibly non-naturally occurring amino acid (e.g., D-type amino acid).

The GLP-1 variant means a peptide possessing an insulinotropic function, which has one or more amino acid sequences different from those of a native GLP-1.

The exendin 3 and the exendin 4 are insulinotropic peptides consisting of 39 amino acids, which have a 53% amino acid sequence homology with GLP-1. The amino acid sequences of the exendin-3 and the exendin-4 are as follows:

```
Exendin-3
                                          (SEQ ID NO: 2)
HSDGT FTSDL SKQME EEAVR LFIEW LKNGG PSSGA PPPS Exendin-4
                                          (SEQ ID NO: 3)
HGEGT FTSDL SKQME EEAVR LFIEW LKNGG PSSGA PPPS
```

The exendin agonist means a compound reacting with receptors in-vivo and having equal biological activity to that of exendin, which is irrelevant to the structure of exendin. The exendin derivative means a peptide having at least 80% amino acid sequence homology with the native exendin, which may have some groups on the amino acid residue chemically substituted (e.g., alpha-methylation, alpha-hydroxylation), deleted (e.g., deamination), or modified (e.g., N-methylation), and has an insulinotropic function.

The exendin fragment means a fragment having one or more amino acids added or deleted at the N-terminus or the C-terminus of the native exendin, in which non-naturally occurring amino acids (for example, D-type amino acid) can be added, and has an insulinotropic function.

The exendin variant means a peptide having at least one amino acid sequence different from that of the native exendin, in which has an insulinotropic function.
Each of the preparation methods for the exendin agonist, derivative, the fragment, and the variant can be used individually or in combination. For example, the present invention includes an insulinotropic peptide having an amino acid sequence which have at least one different amino acids from those of native insulinotropic peptide, and having the amino acid residue at the N-terminus deaminated.

In a specific embodiment, the native insulinotropic peptide used in the present invention, and the modified insulinotropic peptide can be synthesized using a solid phase synthesis method, and most of the native peptides including a native insulinotropic peptide can be produced by a recombination technology.

Further, the insulinotropic peptide used in the present invention can bind to the non-peptidyl polymer on various sites.

The peptide conjugate prepared according to the present invention can have an activity which varies depending on the sites to be linked to the insulinotropic peptide.
For example, it can be coupled with an N-terminus, and other terminus other than the N-terminus, such as a C-terminus, respectively, which indicates difference in the in vitro activity. The aldehyde reactive group selectively binds to an N-terminus at a low pH, and can bind to a lysine residue to form a covalent bond at a high pH, such as pH 9.0. A pegylation reaction is allowed to proceed with varying pH, and then a positional isomer can be separated from the reaction mixture using an ion exchange column.

If the insulinotropic peptide is to be coupled at a site other than the N-terminus which is an important site for the in-vivo activity, a reactive thiol group can be introduced to the site of amino acid residue to be modified in the native amino acid sequence to form a covalent bond using a maleimide linker at the non-peptidyl polymer.

If the insulinotropic peptide is to be coupled at a site other than the N-terminus which is an important site for the in-vivo activity, a reactive amine group can be introduced to the site of amino acid residue to be modified in the native amino acid sequence to form a covalent bond using an aldehyde linker at the non-peptidyl polymer.

When the aldehyde linker at the non-peptidyl polymer is used, it is reacted with an amino group at the N-terminus and the lysine residue, and a modified form of the insulinotropic peptide can be used to selectively increase the reaction yield. For example, only one amine group to be reacted can be retained on a desired site, using an N-terminus blocking method, a lysine residue substituting method, a method for introducing an amine group at a carboxyl terminus, or the like, thereby increasing the yield of pegylation and coupling reactions. The methods for protecting the N-terminus include dimethylation, as well as methylation, deamination, acetylation, etc., but are not limited to such alkylation methods.

In one preferable embodiment, the insulinotropic peptide conjugate of the present invention is an insulinotropic peptide conjugate, in which an immunoglobulin Fc region specifically binds to an amine group other than ones at the N-terminus of the insulinotropic peptide.

In one specific embodiment, the present inventors induced a pegylation of a native exendin-4 at pH 9.0, to selectively couple the PEG to the lysine residue of the insulinotropic peptide. Alternatively, to pegylate at Lys residue, the pegylation of the exendin-4 derivatives having the N-terminus deleted or protected was performed at pH 7.5. The pegylation at the N-terminus was blocked, either by deleting the alpha amine group of the N-terminal histidine, by substituting the N-terminal amine group with hydroxyl group, by modifying the alpha amine group of N-terminal histidine with two methyl groups, or by deleting the alpha carbon of the first amino acid (histidine) and the N-terminal amine group linked thereto to leave the imidazo-acetyl group, and etc. Such derivatives were represented by the following Chemical Formulas:

<Chemical Formula 1>

(a)

Des-amino-histidyl
(DA)-Exendin-4

(b)

Beta-hydroxy-imidazopropyl
(HY)-Exendin-4

(c)

Imidazoacetyl
(CA)-Exendin-4

Dimethyl-histidyl
(DM)-Exendin-4

Figure 14:
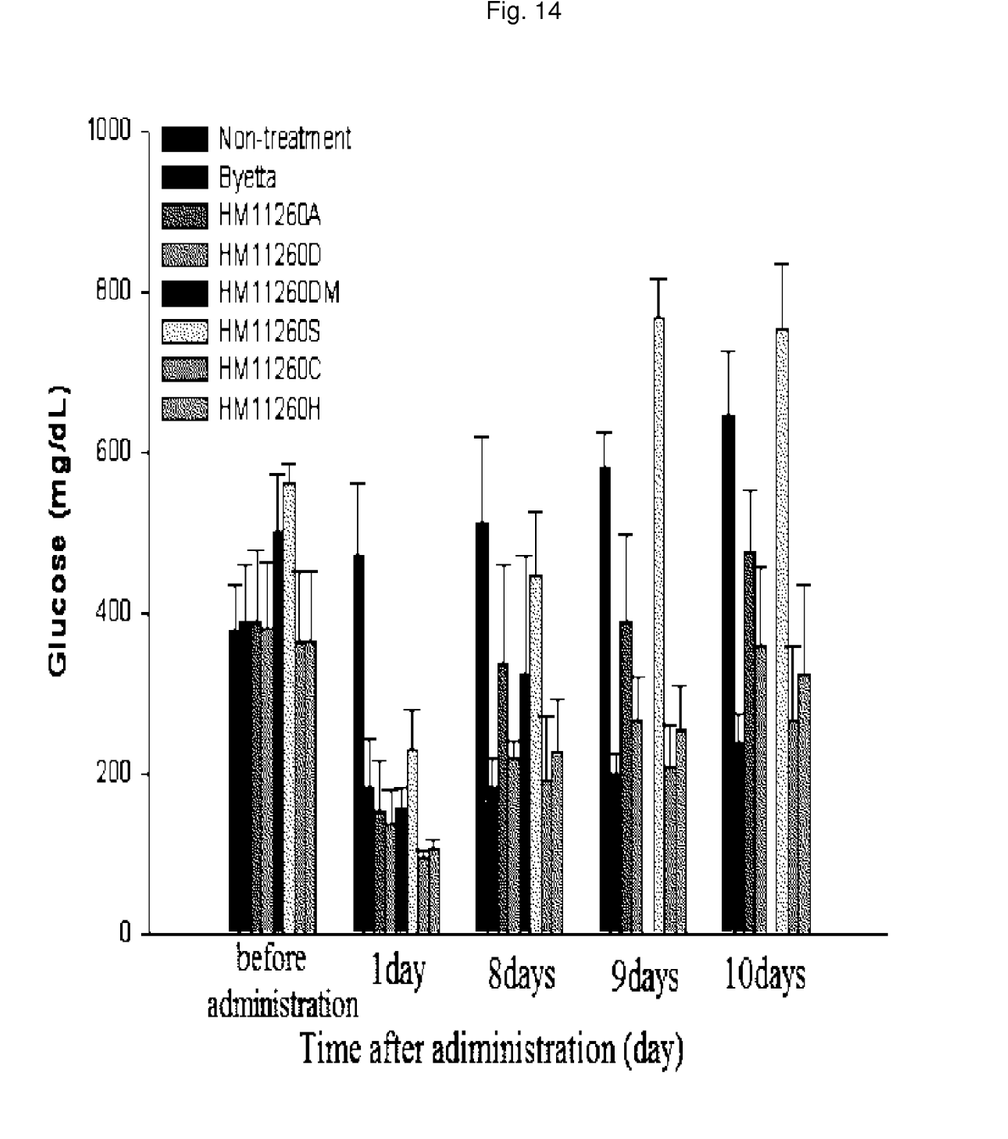
FIG. 14 shows the results of measurement of the glucose concentration reducing effect in blood of a des-amino-histidyl exendin-4(Lys)-PEG-immunoglobulin Fc conjugate.

Unlike the N-terminal coupling, when the PEG was coupled to the lysine residue rather than the N-terminus, the in vitro activity was maintained at about 8.5% (Table 1). Further, even if the Fc conjugates of des-amino-histidyl exendin-4 (hereinafter, referred to as DA-exendin-4) prepared by deleting N-terminal amine group of exendin-4, beta-hydroxyl-imidazol propionyl exendin-4 (hereinafter, referred to as HY-exendin-4) prepared by substituting N-terminal amine group of exendin-4 with hydroxyl group, dimethyl histidyl exendin-4 (hereinafter, referred to as DM-exendin-4) prepared by modifying N-terminal amine group of exendin-4 with two methyl group, and imidazolacetyl-exendin-4 (hereinafter, referred to as CA-exendin-4) prepared by deleting α-carbon of the first histidine of exendin-4 and the N-terminal amine group linked thereto, showed comparable in-vitro activity and the blood half life to the native exendin-4 conjugate (Table 1), these conjugates showed unexpectedly high in-vivo duration of efficacy (FIG. 14). DM-exendin-4-immunoglobulin Fc conjugate, DA-exendin-4-immunoglobulin Fc conjugate, CA-exendin-4-immunoglobulin Fc conjugate and HY exendin-4-immunoglobulin Fc conjugate prepared according to the present invention showed an increased blood half-life of 50 hours or more. The titer reduction was also minimized by coupling to the Lys residue which does not affect the activity of the peptide. In addition, an unexpectedly high glucose lowering activity was observed by removing the amine group or alpha carbon at the N-terminus.

The immunoglobulin Fc region is safe for use as a drug carrier because it is a biodegradable polypeptide that is in vivo metabolized. Also, the immunoglobulin Fc region has a relatively low molecular weight, as compared to the whole immunoglobulin molecules, and thus, it is advantageous in the preparation, purification and yield of the conjugate. Since the immunoglobulin Fc region does not contain a Fab fragment, whose amino acid sequence differs according to the antibody subclasses and which thus is highly non-homogenous, it can be expected that the immunoglobulin Fc region may greatly increase the homogeneity of substances and be less antigenic.

The insulinotropic peptide used in the present invention is linked with a carrier substance and non-peptidyl polymer.

The carrier substance which can be used in the present invention may be selected from the group consisting of an immunoglobulin Fc region, an albumin, a transferrin, and a PEG, and preferably an immunoglobulin Fc region.

The term "immunoglobulin Fc region" as used herein, refers to the heavy-chain constant region 2 ($C_H2$) and the heavy-chain constant region 3 ($C_H3$) of an immunoglobulin, and not the variable regions of the heavy and light chains, the heavy-chain constant region 1 ($C_H1$) and the light-chain constant region 1 ($C_L1$) of the immunoglobulin. It may further include a hinge region at the heavy-chain constant region. Also, the immunoglobulin Fc region of the present invention may contain a part or all of the Fc region including the heavy-chain constant region 1 ($C_H1$) and/or the light-chain constant region 1 ($C_L1$), except for the variable regions of the heavy and light chains, as long as it has a physiological function substantially similar to or better than the native protein. Also, the Ig Fc region may be a fragment having a deletion in a relatively long portion of the amino acid sequence of $C_H2$ and/or $C_H3$. That is, the immunoglobulin Fc region of the present invention may comprise 1) a $C_H1$ domain, a $C_H2$ domain, a $C_H3$ domain and a $C_H4$ domain, 2) a $C_H1$ domain and a $C_H2$ domain, 3) a $C_H1$ domain and a $C_H3$ domain, 4) a $C_H2$ domain and a $C_H3$ domain, 5) a combination of one or more domains and an immunoglobulin hinge region (or a portion of the hinge region), and 6) a dimer of each domain of the heavy-chain constant regions and the light-chain constant region.

The immunoglobulin Fc region of the present invention includes a native amino acid sequence, and a sequence derivative (mutant) thereof. An amino acid sequence derivative is a sequence that is different from the native amino acid sequence due to a deletion, an insertion, a non-conservative or conservative substitution or combinations thereof of one or more amino acid residues. For example, in an IgG Fc, amino acid residues known to be important in binding, at positions 214 to 238, 297 to 299, 318 to 322, or 327 to 331, may be used as a suitable target for modification. Also, other various derivatives are possible, including one in which a region capable of forming a disulfide bond is deleted, or certain amino acid residues are eliminated at the N-terminus of a native Fc form or a methionine residue is added thereto. Further, to remove effector functions, a deletion may occur in a complement-binding site, such as a C1q-binding site and an ADCC (antibody dependent cell mediated cytotoxicity) site. Techniques of preparing such sequence derivatives of the immunoglobulin Fc region are disclosed in International Pat. Publication Nos. WO 97/34631 and WO 96/32478.

Amino acid exchanges in proteins and peptides, which do not generally alter the activity of molecules are known in the art (H. Neurath, R. L. Hill, The Proteins, Academic Press, New York, 1979). The most commonly occurring exchanges are Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly in both directions.

The Fc region, if desired, may be modified by phosphorylation, sulfation, acrylation, glycosylation, methylation, farnesylation, acetylation, amidation, and the like.

The aforementioned Fc derivatives are derivatives that have a biological activity identical to the Fc region of the present invention or improved structural stability, for example, against heat, pH, or the like.

In addition, these Fc regions may be obtained from native forms isolated from humans and other animals including cows, goats, swine, mice, rabbits, hamsters, rats and guinea pigs, or may be recombinants or derivatives thereof, obtained from transformed animal cells or microorganisms. Herein, they may be obtained from a native immunoglobulin by isolating whole immunoglobulins from human or animal organisms and treating them with a proteolytic enzyme. Papain digests the native immunoglobulin into Fab and Fc regions, and pepsin treatment results in the production of pF'c and F(ab)2 fragments. These fragments may be subjected, for example, to size exclusion chromatography to isolate Fc or pF'c.

Preferably, a human-derived Fc region is a recombinant immunoglobulin Fc region that is obtained from a microorganism.

In addition, the immunoglobulin Fc region of the present invention may be in the form of having native sugar chains, increased sugar chains compared to a native form or decreased sugar chains compared to the native form, or may be in a deglycosylated form. The increase, decrease or removal of the immunoglobulin Fc sugar chains may be achieved by methods common in the art, such as a chemical method, an enzymatic method and a genetic engineering method using a microorganism. The removal of sugar chains from an Fc region results in a sharp decrease in binding affinity to the C1q part of the first complement component C1 and a decrease or loss in antibody-dependent cell-mediated cytotoxicity or complement-dependent cytotoxicity, thereby not inducing unnecessary immune responses in-vivo. In this regard, an immunoglobulin Fc region in a deglycosylated or aglycosylated form may be more suitable to the object of the present invention as a drug carrier.

As used herein, the term "deglycosylation" refers to enzymatically remove sugar moieties from an Fc region, and the term "aglycosylation" means that an Fc region is produced in an unglycosylated form by a prokaryote, preferably *E. coli*.

On the other hand, the immunoglobulin Fc region may be derived from humans or other animals including cows, goats, swine, mice, rabbits, hamsters, rats and guinea pigs, and preferably humans. In addition, the immunoglobulin Fc region may be an Fc region that is derived from IgG, IgA, IgD, IgE and IgM, or that is made by combinations thereof or hybrids thereof. Preferably, it is derived from IgG or IgM, which is among the most abundant proteins in human blood, and most preferably from IgG, which is known to enhance the half-lives of ligand-binding proteins.

On the other hand, the term "combination" as used herein, means that polypeptides encoding single-chain immunoglobulin Fc regions of the same origin are linked to a single-chain polypeptide of a different origin to form a dimer or multimer. That is, a dimer or multimer may be formed from two or more fragments selected from the group consisting of IgG Fc, IgA Fc, IgM Fc, IgD Fc, and IgE Fc fragments.

The term "hybrid" as used herein, means that sequences encoding two or more immunoglobulin Fc regions of different origin are present in a single-chain immunoglobulin Fc region. In the present invention, various types of hybrids are possible. That is, domain hybrids may be composed of one to four domains selected from the group consisting of $C_H1$, $C_H2$, $C_H3$ and $C_H4$ of IgG Fc, IgM Fc, IgA Fc, IgE Fc and IgD Fc, and may include the hinge region.

On the other hand, IgG is divided into IgG1, IgG2, IgG3 and IgG4 subclasses, and the present invention includes combinations and hybrids thereof. Preferred are IgG2 and IgG4 subclasses, and most preferred is the Fc region of IgG4 rarely having effector functions such as CDC (complement dependent cytotoxicity).

That is, as the drug carrier of the present invention, the most preferable immunoglobulin Fc region is a human IgG4-derived non-glycosylated Fc region. The human-derived Fc region is more preferable than a non-human derived Fc region, which may act as an antigen in the human body and cause undesirable immune responses such as the production of a new antibody against the antigen.

The term "non-peptidyl polymer" as used herein, refers to a biocompatible polymer including two or more repeating units linked to each other by any covalent bond excluding a peptide bond.

The non-peptidyl polymer which can be used in the present invention may be selected form the group consisting of polyethylene glycol, polypropylene glycol, copolymers of ethylene glycol and propylene glycol, polyoxyethylated polyols, polyvinyl alcohol, polysaccharides, dextran, polyvinyl ethyl ether, biodegradable polymers such as PLA (polylactic acid) and PLGA (polylactic-glycolic acid), lipid polymers, chitins, hyaluronic acid, and combinations thereof, and preferred is polyethylene glycol. Also, derivatives thereof well known in the art and being easily prepared within the skill of the art are included in the scope of the present invention.

The peptide linker which is used in the fusion protein obtained by a conventional inframe fusion method has drawbacks that it is easily in-vivo cleaved by a proteolytic enzyme, and thus a sufficient effect of increasing the blood half-life of the active drug by a carrier cannot be obtained as expected. However, in the present invention, a polymer having resistance to the proteolytic enzyme can be used to maintain the blood half-life of the peptide to be similar to that of the carrier. Therefore, any non-peptidyl polymer which can be used in the present invention can be used without any limitation, as long as it is a polymer having the aforementioned function, that is, a polymer having resistance to the in-vivo proteolytic enzyme. The non-peptidyl polymer preferably has a molecular weight in the range of 1 to 100 kDa, and preferably of 1 to 20 kDa. Also, the non-peptidyl polymer of the present invention, linked to the immunoglobulin Fc region, may be one polymer or a combination of different types of polymers.

The non-peptidyl polymer used in the present invention has a reactive group capable of binding to the immunoglobulin Fc region and the protein drug.

The non-peptidyl polymer has a reactive group at both ends, which is preferably selected from the group consisting of a reactive aldehyde group, a propionaldehyde group, a butyraldehyde group, a maleimide group and a succinimide derivative. The succinimide derivative may be succinimidyl propionate, hydroxy succinimidyl, succinimidyl carboxymethyl, or succinimidyl carbonate. In particular, when the non-peptidyl polymer has a reactive aldehyde group at both ends, it is effective in linking at both ends with a physiologically active polypeptide and an immunoglobulin with minimal non-specific reactions. A final product generated by reductive alkylation by an aldehyde bond is much more stable than when linked by an amide bond. The aldehyde reactive group selectively binds to an N-terminus at a low pH, and can bind to a lysine residue to form a covalent bond at a high pH, such as pH 9.0.

The reactive groups at both ends of the non-peptidyl polymer may be the same or different. For example, the non-peptide polymer may possess a maleimide group at one end and at the other end, an aldehyde group, a propionaldehyde group or a butyraldehyde group. When a polyethylene glycol having a reactive hydroxy group at both ends thereof is used as the non-peptidyl polymer, the hydroxy group may be activated to various reactive groups by known chemical reactions, or a polyethylene glycol having a commercially available modified reactive group may be used so as to prepare the insulinotropic peptide conjugate of the present invention.

The insulinotropic peptide conjugate of the present invention maintains the conventional in-vivo activities of the insulinotropic peptide, such as promotion of synthesis and secretion of insulin, appetite control, weight loss, increase in the beta cell sensitivity to glucose in blood, promotion of beta cell proliferation, delayed gastric emptying, and glucagon suppression, and further remarkably increases the blood half-life of the insulinotropic peptide, and hence the in-vivo efficacy sustaining effect of the peptide, it is useful to treat diabetes, obesity, acute coronary syndrome, or polycystic ovary syndrome.

In another embodiment, the present invention provides a method for preparing an insulinotropic peptide conjugate, comprising the steps of:

(1) covalently linking a non-peptidyl polymer having a reactive group selected from the group consisting of aldehyde, maleimide, and succinimide derivatives at both ends thereof, with an amine group or thiol group of the insulinotropic peptide;

(2) isolating a conjugate comprising the insulinotropic peptide from the reaction mixture of (1), in which the non-peptidyl polymer is linked covalently to a site other than the N-terminus; and (3) covalently linking an immunoglobulin Fc region to the other end of the non-peptidyl polymer of the isolated conjugate to produce a peptide conjugate comprising the immunoglobulin Fc region and the insulinotropic peptide, which are linked to each end of the non-peptidyl polymer.

The term "conjugate" as used herein, refers to an intermediate prepared by covalently linking the non-peptidyl polymer with the insulinotropic peptide, and subsequently the immunoglobulin Fc region is linked to the other end of the non-peptidyl polymer.

In a preferable embodiment, the present invention provides a method for preparing an insulinotropic peptide conjugate, comprising the steps of:

(1) covalently linking a non-peptidyl polymer having an aldehyde reactive group at both ends thereof with the lysine residue of the insulinotropic peptide;

(2) isolating a conjugate comprising the insulinotropic peptide from the reaction mixture of (1), in which the non-peptidyl polymer is linked covalently to the lysine residue; and (3) covalently linking an immunoglobulin Fc region to the other end of the non-peptidyl polymer of the isolated conjugate to produce a protein conjugate comprising the immunoglobulin Fc region and the insulinotropic peptide, which are linked to each end of the non-peptidyl polymer. More preferably, the non-peptidyl polymer of (1), and the lysine residue of the insulinotropic peptide are linked at pH 7.5 or higher.

In a further embodiment, the present invention provides a pharmaceutical composition for treating diabetes, comprising the insulinotropic peptide conjugate of the present invention.

The pharmaceutical composition comprising the conjugate of the present invention can further comprise a pharmaceutically acceptable carrier. For oral administration, the pharmaceutically acceptable carrier may include a binder, a lubricant, a disintegrator, an excipient, a solubilizer, a dispersing agent, a stabilizer, a suspending agent, a coloring agent, and a perfume. For injectable preparations, the pharmaceutically acceptable carrier may include a buffering agent, a preserving agent, an analgesic, a solubilizer, an isotonic agent, and a stabilizer. For preparations for topical administration, the pharmaceutically acceptable carrier may include a base, an excipient, a lubricant, and a preserving agent. The pharmaceutical composition of the present invention may be formulated into a variety of dosage forms in combination with the aforementioned pharmaceutically acceptable carriers. For example, for oral administration, the pharmaceutical composition may be formulated into tablets, troches, capsules, elixirs, suspensions, syrups or wafers. For injectable preparations, the pharmaceutical composition may be formulated into an ampule as a single-dose dosage form or a unit dosage form, such as a multidose container. The pharmaceutical composition may be also formulated into solutions, suspensions, tablets, pills, capsules and long-acting preparations.

On the other hand, examples of the carrier, the excipient, and the diluent suitable for the pharmaceutical formulations include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oils. In addition, the pharmaceutical formulations may further include fillers, anti-coagulating agents, lubricants, humectants, perfumes, and antiseptics.

The conjugate according to the present invention is useful to treat diabetes, obesity, acute coronary syndrome, or polycystic ovary syndrome. Accordingly, a pharmaceutical composition comprising the conjugate can be administered for the treatment of the diseases.

The term "administration" as used herein, means introduction of a predetermined amount of a substance into a patient by a certain suitable method. The conjugate of the present invention may be administered via any of the common routes, as long as it is able to reach a desired tissue. A variety of modes of administration are contemplated, including intraperitoneally, intravenously, intramuscularly, subcutaneously, intradermally, orally, topically, intranasally, intrapulmonarily and intrarectally, but the present invention is not limited to these exemplified modes of administration. However, since peptides are digested upon oral administration, active ingredients of a composition for oral administration should be coated or formulated for protection against degradation in the stomach. Preferably, the present composition may be administered in an injectable form. In addition, the pharmaceutical composition of the present invention may be administered using a certain apparatus capable of transporting the active ingredients into a target cell.

The administration frequency and dose of the pharmaceutical composition of the present invention can be determined by several related factors including the types of diseases to be treated, administration routes, the patient's age, gender, weight and severity of the illness, as well as by the types of the drug as an active component. Since the pharmaceutical composition of the present invention has excellent duration of in-vivo efficacy and titer, it can remarkably reduce the administration frequency and dose of pharmaceutical drugs of the present invention.

A better understanding of the present invention may be obtained through the following examples which are set forth to illustrate, but are not to be construed as the limit of the present invention.

MODE FOR INVENTION

Example 1

Pegylation of Exendin-4 and Isolation of Positional Isomer 3.4K PropionALD(2) PEG (PEG having two propionaldehyde groups, IDB Inc., South Korea) and the N-terminus of the exendin-4 (AP, USA) were subjected to pegylation by reacting the peptide and the PEG at 4° C. for 90 min at a molar ratio of 1:15, with a peptide concentration of 3 mg/ml. At this time, the reaction was performed in a NaOAc buffer at pH 4.0 at a concentration of 100 mM, and 20 mM SCB (NaCNBH3) as a reducing agent was added thereto to perform the reaction. 3.4K PropionALD(2) PEG and the lysine (Lys) residue of the exendin-4 were subjected to pegylation by reacting the peptide and the PEG at 4° C. for 3 hours at a molar ratio of 1:30, with a peptide concentration of 3 mg/ml. At this time, the reaction was performed in a Na-Phosphate buffer at pH 9.0 at a concentration of 100 mM, and 20 mM SCB as a reducing agent was added thereto to perform the reaction. A monopegylated peptide was purified from each of the reaction solutions using SOURCE Q (XK 16 ml, Amersham Biosciences), and isomers were isolated using SOURCE S (XK 16 ml, Amersham Biosciences). It was found that a peak for pegylated N-terminus was found earlier, and then two peaks for pegylated lysine residues were found in turn. The pegylated regions of eluted peaks were confirmed by peptide mapping method. The Lys12-pegylated conjugate was eluted earlier, the Lys 27-pegylated conjugate was eluted in the last portion, and a positional isomer of N-terminus and a positional isomer of Lys 12 are completely isolated from each other.
Column: SOURCE Q (XK 16 ml, Amersham Biosciences)
Flow rate: 2.0 ml/min
Gradient: A 0→40% 80 min B (A: 20 mM Tris pH 8.5, B: A+0.5 M NaCl)
Column: SOURCE S (XK 16 ml, Amersham Biosciences)
Flow rate: 2.0 ml/min
Gradient: A 0→100% 50 min B (A: 20 mM citric acid pH 3.0, B: A+0.5 M KCl)

Example 2

Preparation of Exendin-4(N)-PEG-Immunoglobulin Fc Conjugate

Figure 1:
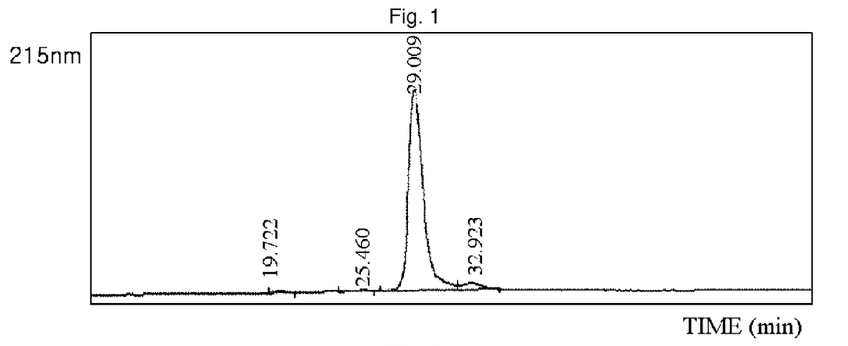
FIG. 1 shows the results of reverse phase HPLC for measurement of the purity of a native exendin-4(N)-PEG-immunoglobulin Fc conjugate.

Using the same method as described in EXAMPLE 1, 3.4K PropionALD(2) PEG and the N-terminus of the exendin-4 were reacted, and only the N-terminal isomers were purified, and then coupled with immunoglobulin Fc. The reaction was performed at a ratio of peptide:immunoglobulin Fc of 1:8, and a total concentration of proteins of 50 mg/ml at 4° C. for 17 hours. The reaction was performed in a solution of 100 mM K—P (pH 6.0), and 20 mM SCB as a reducing agent was added thereto. The coupling reaction solution was purified using two purification columns. First, SOURCE Q (XK 16 ml, Amersham Biosciences) was used to remove a large amount of immunoglobulin Fc which had not participated in the coupling reaction. Using 20 mM Tris (pH 7.5) and 1 M NaCl with salt gradients, the immunoglobulin Fc having relatively weak binding power was eluted earlier, and then the exendin-4-immunoglobulin Fc was eluted. Through this first purification procedure, the immunoglobulin Fc was removed to some degree, but since the immunoglobulin Fc and the exendin-4-immunoglobulin Fc have similar binding powers to each other in the ion exchange column, they could not be completely separated from each other. Accordingly, secondary purification was performed using hydrophobicity of each of two materials. Using 20 mM Tris (pH7.5) 1.5 M ammonium sulfate in SOURCE ISO(HR 16 ml, Amersham Biosciences), the first purified samples were coupled, and the sample was eluted with gradually reducing the concentration of ammonium sulfate. In the HIC Column, the immunoglobulin Fc having weak binding power was eluted earlier, and then the exendin-4-immunoglobulin Fc sample having strong binding power was eluted. Since they have prominently different hydrophobicity, they can be more easily separated from each other than in the ion exchange column. However, because excess amounts of immunoglobulin Fc is used due to the difference of molar ratio, high purity was not obtainable using only HIC column. The purity measured by reverse phase HPLC was 91.6%. (FIG. 1)
Column: SOURCE Q (XK 16 ml, Amersham Biosciences)
Flow rate: 2.0 ml/min
Gradient: A 0→25% 70 min B (A: 20 mM Tris pH7.5, B: A+1 M NaCl)
Column: SOURCE ISO(HR 16 ml, Amersham Biosciences)
Flow rate: 7.0 ml/min
Gradient: B 100→0% 60 min B (A: 20 mM Tris pH7.5, B: A+1.5 M ammonium sulfate)

Example 3

Preparation of Exendin-4(Lys27)-PEG-Immunoglobulin Fc Conjugate

Figure 2:
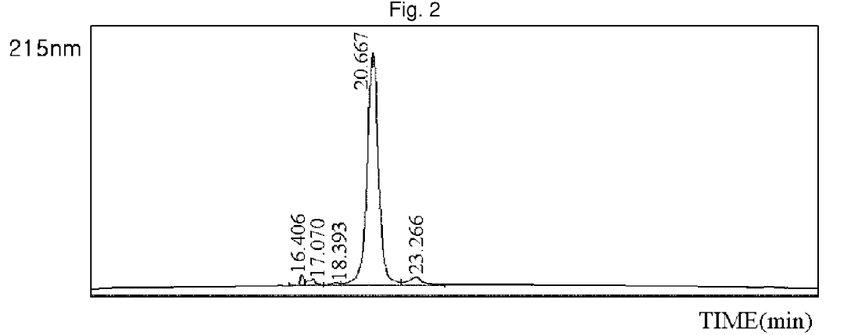
FIG. 2 shows the results of reverse phase HPLC for measurement of the purity of a native exendin-4(Lys)-PEG-immunoglobulin Fc conjugate.

Using the same method as described in EXAMPLE 1, 3.4K PropionALD(2) PEG and the lysine (Lys) of the exendin-4 were reacted, and only the Lys isomers were purified, and then coupled with immunoglobulin Fc. Among the two isomer peaks, the last isomer peak (positional isomer of Lys27), which has more reaction and which is easily distinguishable from the N-terminal isomer peaks, was used for the coupling reaction. The reaction was performed at a ratio of peptide:immunoglobulin Fc of 1:8, and a total concentration of proteins of 50 mg/ml at 4° C. for 16 hours. The reaction was performed in a solution of 100 mM K—P (pH 6.0), and 20 mM SCB was added as a reducing agent. After the coupling reaction, the two-step purification process using SOURCE Q 16 ml and SOURCE ISO 16 ml was the same as in EXAMPLE 2. The purity measured by reverse phase HPLC was 91.7%. (FIG. 2)

Example 4

Figure 3:
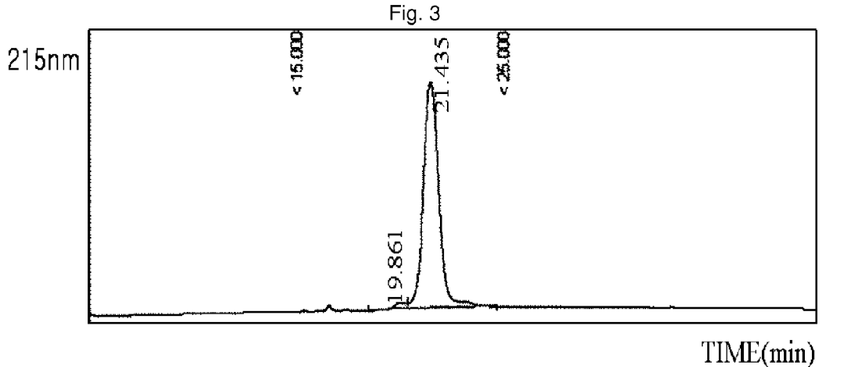
FIG. 3 shows the results of reverse phase HPLC for measurement of the purity of a des-amino-histidyl exendin-4 (Lys)-PEG-immunoglobulin Fc conjugate.

Preparation of Des-amino-histidyl Exendin-4(Lys27)-PEG-Immunoglobulin Fc Conjugate To pegylate 3.4K PropionALD(2) PEG to the lysine (Lys) residue of the des-amino-histidyl exendin-4 (DA-exedin-4, AP, USA), pegylation was performed with by reacting the peptide and the 3.4K PropionALD(2) at 4° C. for 12 hours at a molar ratio of 1:30, with a peptide concentration of 3 mg/ml. The reaction solution was in a Na-Phosphate buffer, pH 7.5 at 100 mM, and 20 mM SCB was added as a reducing agent. A pegylated peptide was purified by the two-step purification process, using SOURCE Q (XK 16 ml, Amersham Biosciences) and SOURCE S (XK 16 ml, Amersham Biosciences). Among the two isomer peaks, the last isomer peak (positional isomer of Lys27), which has more reaction and which is easily distinguishable from the N-terminal isomer peaks, was used for the coupling reaction. The reaction was performed at a ratio of peptide:immunoglobulin Fc of 1:8, at a total proteins concentration of 60 mg/ml, at 4° C. for 20 hours. The reaction was performed in 100 mM K—P (pH 6.0), and 20 mM SCB was added as a reducing agent. The two-step purification process using SOURCE Q 16 ml and SOURCE ISO 16 ml, after the coupling, was the same as described in EXAMPLE 2. The purity measured by reverse phase HPLC was 95.8%. (FIG. 3)
Column: SOURCE Q (XK 16 ml, Amersham Biosciences)
Flow rate: 2.0 ml/min
Gradient: A 0→20% 70 min B (A: 20 mM Tris pH9.0, B: A+1 M NaCl)
Column: SOURCE S (XK 16 ml, Amersham Biosciences)
Flow rate: 2.0 ml/min
Gradient: A 0→50% 50 min B (A: 20 mM Citric acid pH3.0, B: A+1 M KCl)

Example 5

Figure 4:
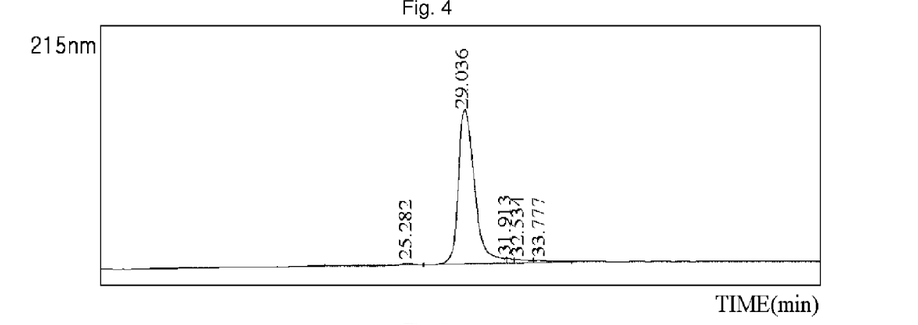
FIG. 4 shows the results of reverse phase HPLC for measurement of the purity of a (2-Hydroxy-3-(1H-imidazol-4-yl) propionyl)exendin-4(Lys)-PEG-immunoglobulin Fc conjugate.

Preparation of Hydroxyl-imidazo-propionyl Exendin-4(Lys27)-PEG-Immunoglobulin Fc Conjugate Using the same method as described in EXAMPLE 4, 3.4K PropionALD(2) PEG was reacted with the lysine (Lys) residue of the beta-hydroxy-imidazo-propionyl exendin-4(HY-exendin-4, AP, USA). Among the two isomer peaks, the last isomer peak (positional isomer of Lys27), which has more reaction and which is easily distinguishable from the N-terminal isomer peaks, was used for the coupling reaction. The reaction was performed at a ratio of peptide:immunoglobulin Fc of 1:8, and a total protein concentration of 60 mg/ml, at 4° C. for 20 hours. The reaction was performed in 100 mM K—P (pH 6.0), and 20 mM SCB was added as a reducing agent. After the coupling reaction, the two-step purification was performed using SOURCE Q 16 ml and SOURCE ISO 16 ml, as described in EXAMPLE 2. The purity measured by reverse phase HPLC was 93.9%. (FIG. 4)

Example 6

Preparation of Imidazo-acetyl Exendin-4(Lys27)-PEG-Immunoglobulin Fc Conjugate

Figure 5:
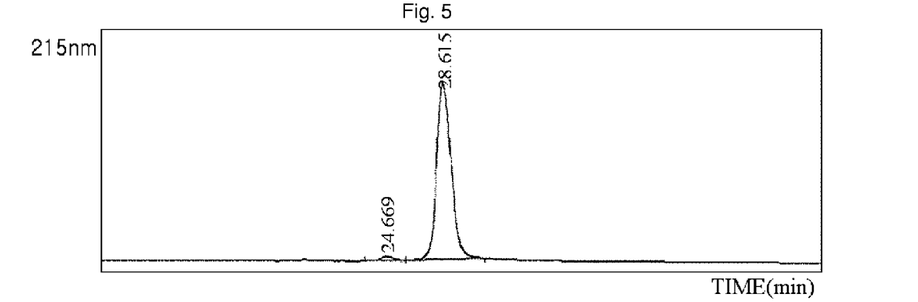
FIG. 5 shows the results of reverse phase HPLC for measurement of the purity of a (2-(1H-imidazol-4-yl)acetyl)exendin-4(Lys)-PEG-immunoglobulin Fc conjugate.

Using the same method as described in EXAMPLE 4, 3.4K PropionALD(2) PEG was reacted with the lysine (Lys) residue of the imidazo-acetyl exendin-4(CA-exendin-4, AP, USA). Among the two isomer peaks, the last isomer peak (positional isomer of Lys27), which has more reaction and which is easily distinguishable from the N-terminal isomer peaks, was used for the coupling reaction. The reaction was performed at a ratio of peptide:immunoglobulin Fc of 1:8, and a total protein concentration of 60 mg/ml, at 4° C. for 20 hours. The reaction was performed in 100 mM K—P (pH 6.0), and 20 mM SCB was added as a reducing agent. After the coupling reaction, the two-step purification process using SOURCE Q 16 ml and SOURCE ISO 16 ml, as described in EXAMPLE 2. The purity measured by reverse phase HPLC was 95.8%. (FIG. 5)

Example 7

Figure 6:
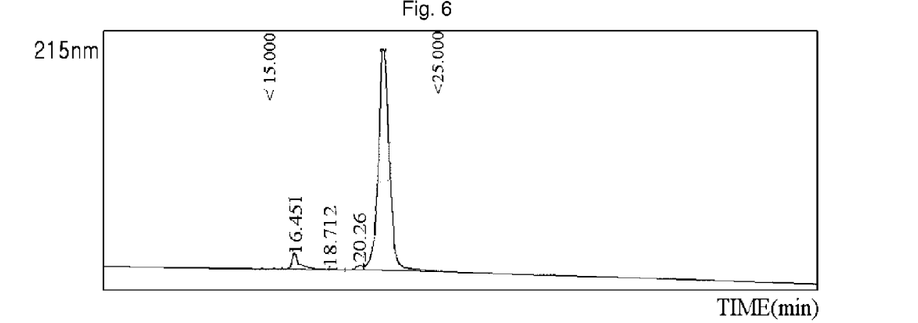
FIG. 6 shows the results of reverse phase HPLC for measurement of the purity of a Ser12 mutated des-amino-histidyl exendin-4(Lys)-PEG-immunoglobulin Fc conjugate.

Preparation of Ser12 Mutated DA Exendin-4(Lys27)-PEG-Immunoglobulin Fc Conjugate 3.4K PropionALD(2) PEG and the lysine (Lys) residue of the Ser12 mutated DA exendin-4 were subjected to pegylation by reacting the peptide and the 3.4K PropionALD(2) at 25° C. for 3 hours at a molar ratio of 1:30, with a peptide concentration of 3 mg/ml. At this time, the reaction was performed in a Na-Phosphate buffer at pH 7.5 at a concentration of 100 mM, and 20 mM SCB as a reducing agent was added thereto to perform the reaction. The purification process of a mono-pegylated peptide using SOURCE Q (XK 16 ml, Amersham Biosciences) without using SOURCE S (XK 16 ml, Amersham Bioscience) was performed as described in EXAMPLE 4. The reaction was performed at a ratio of peptide:immunoglobulin Fc of 1:8, and a total concentration of proteins of 60 mg/ml at 4° C. for 20 hours. The reaction was performed in a solution of 100 mM K—P (pH 6.0), and 20 mM SCB was added as a reducing agent. Because Ser12 mutated DA exendin-4 has much stronger anionic property, the excess amounts of immunoglobulin Fc, which were not participated in the reaction, were eliminated effectively by the purification process using SOURCE Q only. Accordingly, the purification process using SOURCE ISO was omitted, and the condition of purification process using SOURCE Q was the same as in EXAMPLE 2. The purity measured by reverse phase HPLC was 92.5%. (FIG. 6)

Example 8

Figure 7:
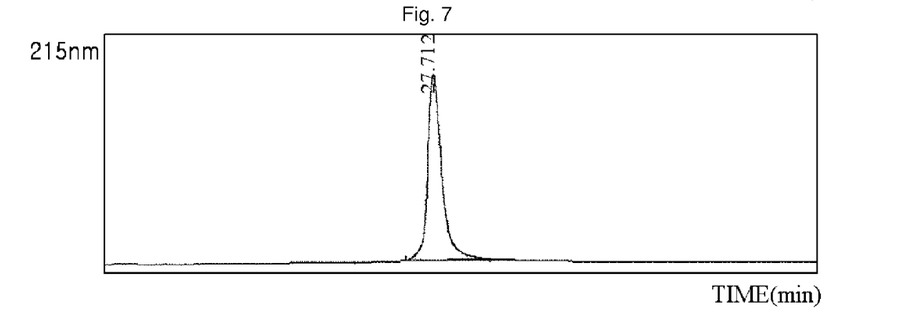
FIG. 7 shows the results of reverse phase HPLC for measurement of the purity of an Arg12-mutated des-amino-histidyl exendin-4(Lys)-PEG-immunoglobulin Fc conjugate.

Preparation of Arg12 Mutated DA Exendin-4(Lys27)-PEG-Immunoglobulin Fc Conjugate Using the same method as described in EXAMPLE 7, 3.4K PropionALD(2) PEG was reacted with the lysine (Lys) residue of the Arg12 mutated DA exendin-4(AP, USA), and purified. Then, coupling process was proceeded. The reaction was performed at a ratio of peptide:immunoglobulin Fc of 1:8, and a total concentration of proteins of 60 mg/ml at 4° C. for 20 hours. The reaction was performed in a solution of 100 mM K—P (pH 6.0), and 20 mM SCB was added as a reducing agent. After the coupling reaction, the two-step purification process using SOURCE Q 16 ml and SOURCE ISO 16 ml was the same as in EXAMPLE 2. The purity measured by reverse phase HPLC was 99.2%. (FIG. 7)

Example 9

Preparation of Des Amino-histidyl Exendin-4(Lys27)-PEG-Albumin Conjugate

Figure 8:
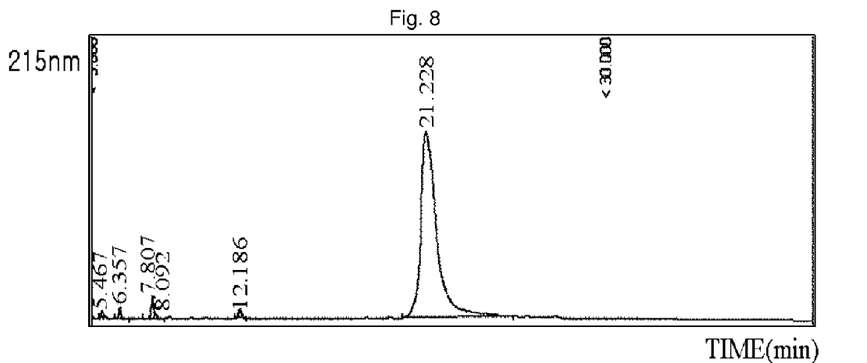
FIG. 8 shows the results of reverse phase HPLC for measurement of the purity of a des-amino-histidyl exendin-4 (Lys)-PEG-human serum albumin (HSA) conjugate.

Using the same method as described in EXAMPLE 4, 3.4K PropionALD(2) PEG was reacted with the lysine (Lys) residue of the des-amino-histidyl exendin-4 (AP, USA), and purified. The reaction was performed at a ratio of peptide:human blood-derived albumin (Green cross, South Korea) as a carrier substance of 1:7, and a total concentration of proteins of 50 mg/ml at 4° C. for 24 hours. The reaction was performed in a solution of 100 mM K—P (pH 6.0), and 20 mM SCB was added as a reducing agent. After the coupling reaction, the two-step purification process using SOURCE Q 16 ml and SOURCE ISO 16 ml was the same as in EXAMPLE 2. The purity measured by reverse phase HPLC was 90.3%. (FIG. 8)

Example 10

Figure 9:
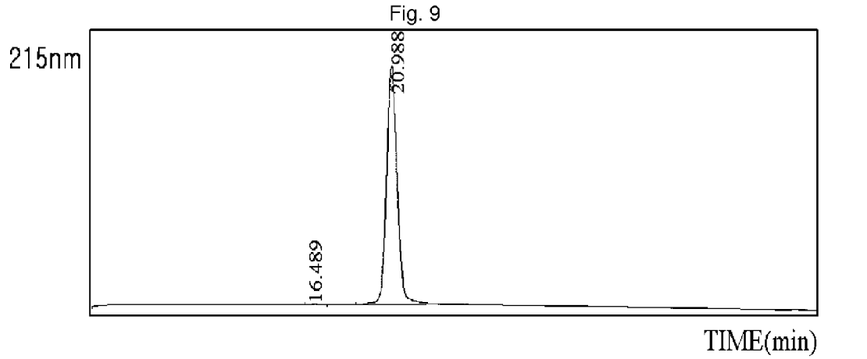
FIG. 9 shows the results of reverse phase HPLC for measurement of the purity of a dimethyl-histidyl exendin-4(Lys)-PEG-immunoglobulin Fc conjugate.

Preparation of Dimethyl-histidyl Exendin-4(Lys27)-PEG-Immunoglobulin Fc Conjugate Using dimethyl-histidyl exendin-4 (DM exendin, AP, USA), dimethyl-histidyl exendin-4(Lys27)-immunoglobulin Fc conjugate was prepared in the same method as described in EXAMPLE 4. The purity measured by reverse phase HPLC was 96.4%. (FIG. 9)

Example 11

Figure 10:
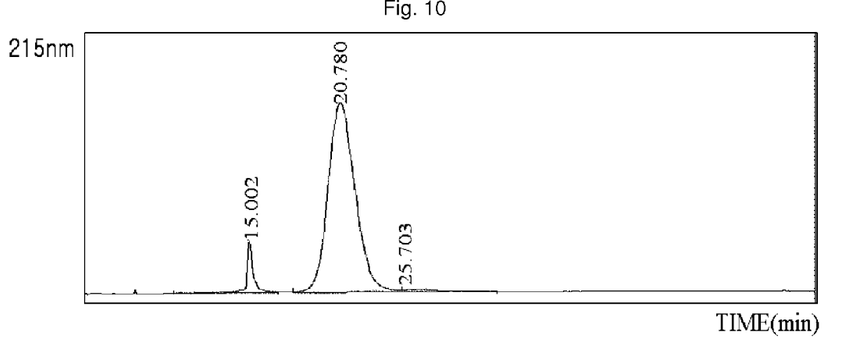
FIG. 10 shows the results of reverse phase HPLC for measurement of the purity of a GLP-1(N)-PEG-immunoglobulin Fc conjugate.

Preparation of GLP-1 (N)-PEG-Immunoglobulin Fc Conjugate 3.4K ButyrALD(2) PEG (PEG having two butyraldehyde groups, Nektar, USA) and the N-terminus of the GLP-1 (AP, USA) were subjected to pegylation by reacting the peptide and the PEG at 4° C. for 90 min at a molar ratio of 1:5, with a peptide concentration of 3 mg/ml. At this time, the reaction was performed in a solution of 100 mM K—P (pH 6.0), and 20 mM SCB (NaCNBH$_3$) as a reducing agent was added thereto. Then, the reaction was performed at a molar ratio of peptide:immunoglobulin Fc of 1:10, and a total concentration of proteins of 50 mg/ml at 4° C. for 16 hours. The reaction was performed in a solution of 100 mM K—P (pH 6.0), and 20 mM SCB was added as a reducing agent. After the coupling reaction, the two-step purification process using SOURCE Q 16 ml and SOURCE ISO 16 ml was the same as in EXAMPLE 2. The purity measured by reverse phase HPLC was 91%. (FIG. 10)

Example 12

Preparation of Des-amino-histidyl-GLP-1(Lys27)-PEG-Immunoglobulin Fc Conjugate

Figure 11:
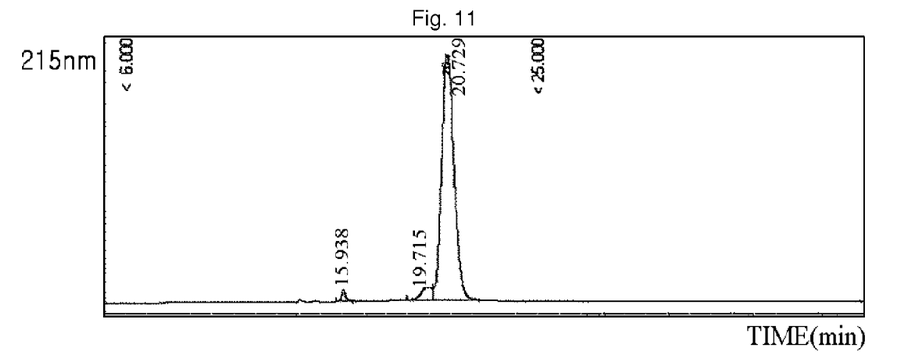
FIG. 11 shows the results of reverse phase HPLC for measurement of the purity of a des-amino-histidyl GLP-1(Lys)-PEG-immunoglobulin Fc conjugate.

3.4K PropionALD(2) PEG and the lysine (Lys) residue of the des-amino-histidyl GLP-1(AP, USA) were subjected to pegylation by reacting the peptide and the 3.4K PropionALD (2) at 4° C. for 4 hours at a molar ratio of 1:30, with a peptide concentration of 3 mg/ml. At this time, the reaction was performed in a Na-Phosphate buffer at pH 7.5 at a concentration of 100 mM, and 20 mM SCB as a reducing agent was added thereto to perform the reaction. The purification process of a mono-pegylated peptide using SOURCE Q (XK 16 ml, Amersham Biosciences) was performed. The reaction was performed at a ratio of peptide:immunoglobulin Fc of 1:6, and a total concentration of proteins of 60 mg/ml at 4° C. for 16 hours. The reaction was performed in a solution of 100 mM K—P (pH 6.0), and 20 mM SCB was added as a reducing agent. After the coupling reaction, the two-step purification process using SOURCE Q 16 ml and SOURCE ISO 16 ml was the same as in EXAMPLE 2. However, the resolution in SOURCE ISO 16 ml was declined because the difference of hydrophobicity between GLP-1 immunoglobulin Fc conjugate and immunoglobulin Fc is less than that between exendin-4 immunoglobulin Fc and immunoglobulin Fc. Accordingly, the purifying process using SOURCE ISO 16 ml column was performed further to the above purification process. The purity measured by reverse phase HPLC was 91.9%. (FIG. 11)

Example 13

Preparation of Conjugate Using ButyrALD Linker Peg

Figure 12:
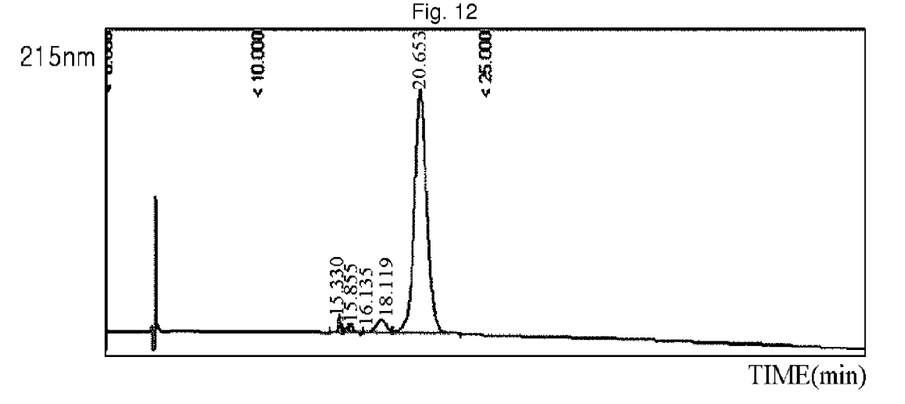
FIG. 12 shows the results of reverse phase HPLC for measurement of the purity of a native exendin-4(Lys)-PEG-immunoglobulin Fc conjugate.
Figure 13:
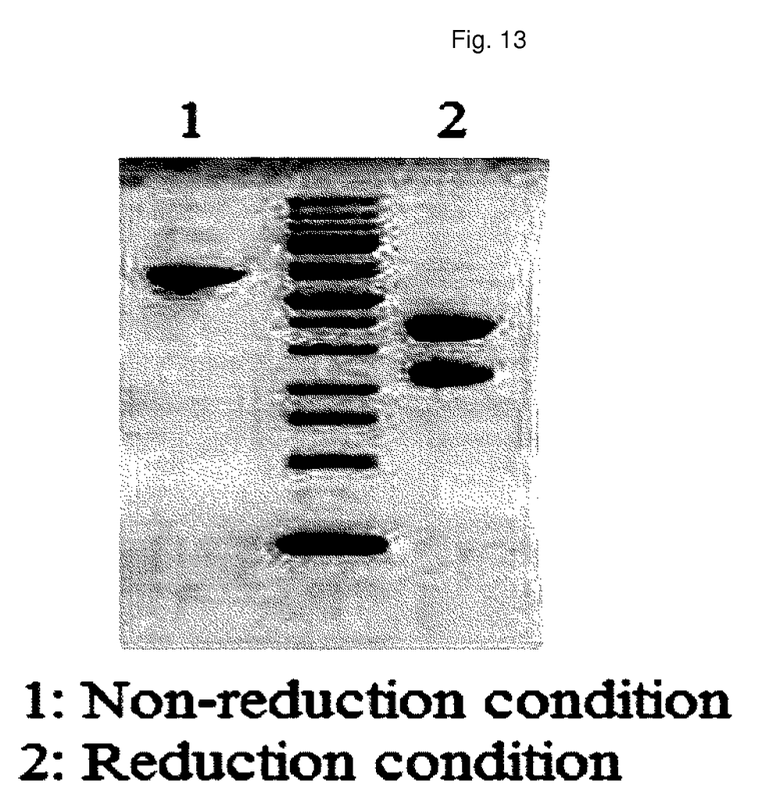
FIG. 13 shows the results of measurement of the purity of a (2-(1H-imidazol-4-yl)acetyl)exendin-4(Lys)-PEG-immunoglobulin Fc conjugate by 12% SDS-PAGE.

Using 3.4K ButyrALD(2) PEG (PEG having two butyraldehyde groups, Nektar, USA), 3.4K-exendin-4 was prepared in the same method as described in EXAMPLE 1. It was coupled immunoglobulin Fc in the same method as described in EXAMPLE 3. The purity measured by reverse phase HPLC was 92.3%. (FIG. 12)

Example 14

Measurement of In-Vitro Activity of Sustained Release Exendin-4

To measure the efficacy of long acting preparation of exendin-4, a method for measuring the in-vitro cell activity was used. Typically, in order to measure the in-vitro activity of GLP-1, insulinoma cells or islet of Langerhans were separated, and whether cAMP's in the cell was increased after treatment of GLP-1 was determined.

For the method for measuring the in-vitro activity used in the present test, RIN-m5F (ATCC.) cells, which are known as Rat insulinoma cells, were used. These cells have GLP-1 receptors, and thus they are often used in the methods for measuring the in-vitro activity in the GLP-1 family. RIN-m5F was treated with GLP-1, exendin-4, and test materials at varying concentrations. The occurrence of cAMP's, which are signaling molecules in the cells, by the test materials, was measured, and hence EC50 values, and compared to each other. The result was shown in Table 1.

TABLE 1

| Test Materials | Blood half-life (hours) | In vitro titer (%) |
|---|---|---|
| Exendin-4 | 0.7 | 100 |
| Exendin-4(N)-PEG-Fc | 62 | <0.2 |
| Exendin-4(Lys27)-PEG-Fc | 61 | 13.2 |
| DM exendin-4(Lys27)-PEG-Fc | 69 | 2.6 |
| DA exendin-4(Lys27)-PEG-Fc | 54 | 13.2 |
| HY exendin-4(Lys27)-PEG-Fc | 52 | 7.6 |
| CA exendin-4(Lys27)-PEG-Fc | 52 | 8.5 |
| Ser12 DA exendin-4(Lys27)-PEG-Fc | N.D. | 2.6 |
| DA exendin-4(Lys27)-PEG-albumin | | 2.0 |
| DA GLP-1(Lys20, 28)-PEG-Fc | 27 | 2.0 |

DM exendin-4: Dimethyl-histidyl exendin-4
DA exendin-4: Des-amino-histidyl exendin-4
HY exendin-4: Beta-hydroxy-imidazo-propionyl exendin-4
CA exendin-4: imidazo-acetyl exendin-4
Ser12 DA exendin-4: DA exendin-4 wherein the 12th lysine residue of the exendin-4 is substituted with Serine
DA GLP-1: des-amino-histidyl-GLP-1
Exendin-4(N)-PEG-Fc: Conjugate in which the N-terminus of the exendin-4 and the Fc region were linked to PEG
Exendin-4(Lys27)-PEG-Fc: Conjugate in which the 27th lysine residue of the exendin-4 and the Fc region were linked to PEG.
DM exendin-4(Lys27)-PEG-Fc: Conjugate in which the 27th lysine residue of the dimethyl histidyl exendin-4 and the Fc region were linked to PEG.
DA exendin-4(Lys27)-PEG-Fc: Conjugate in which the 27th lysine residue of the des-amino-histidyl exendin-4 and the Fc region were linked to PEG.
HY exendin-4(Lys)-PEG-Fc: Conjugate in which the 27th lysine residue of the beta-hydroxy-imidazo-propionyl exendin-4 and the Fc region were linked to PEG.
CA exendin-4(Lys)-PEG-Fc: Conjugate in which the 27th lysine residue of the imidazo-acetyl exendin-4 and the Fc region were linked to PEG.
Ser12 DA exendin-4(Lys27)-PEG-Fc: Conjugate in which the 27th lysine residue of the Ser12 des-amino-histidyl exendin-4 wherein the 12th lysine residue of the exendin-4 is substituted for Serine and the Fc region were linked to PEG.
DA exendin-4(Lys27)-PEG-Albumin: Conjugate in which the 27th lysine residue of the des-amino-histidyl exendin-4 and albumin were linked to PEG.
DA GLP-1(Lys20, 28)-PEG-Fc: Conjugate in which the lysine residue of the des-amino-histidyl GLP-1 and the Fc region were linked to PEG.

Example 15

Test of In-Vivo Efficacy of the Long Acting Exendin-4

To measure the in-vivo efficacy of long acting preparation the exendin-4, a method for measuring the effect of reducing the glucose concentration in blood for db/db mice as diabetic models was used. 100 mcg/kg of long acting exendin-4 preparation was administered once during a 2 week period, and 100 mcg/kg of native exendin-4 was administered per day, to about 6~7-week-old diabetic model mice, without limiting the food supply. After administering the test materials, blood was collected daily, and the change of blood glucose level was measured. Especially, in case of the native exendin-4, the blood glucose concentration was measured after 1 hour of the administration (FIG. 14). The conjugates of the exendin-4 derivatives maintained reduction of the blood glucose concentration for 10 days or longer even when administered once, while the glucose lowering activity of the conjugates of the native exendin-4 disappeared after 8 days.

INDUSTRIAL APPLICABILITY

The insulinotropic peptide conjugate of the present invention has the in-vivo activity which is maintained relatively high, and has remarkably increased blood half-life, and thus it can be desirably employed in the development of long acting formulations of various peptide drugs.

The invention claimed is:

1. An insulinotropic peptide conjugate, comprising an insulinotropic peptide, a non-peptidyl polymer, and an immunoglobulin Fc fragment,
   wherein the insulinotropic peptide and the immunoglobulin Fc fragment are covalently linked through the non-peptidyl polymer;
   wherein the insulinotropic peptide is selected from the group consisting of beta-hydroxy-imidazo-propionyl exendin-4 where the N-terminal amine group of exendin-4 is substituted with hydroxyl group, dimethyl-histidyl exendin-4 where the N-terminal amine group of exendin-4 is modified with two methyl groups, and imidazo-acetyl exendin-4 where the alpha carbon of the first histidine and the N-terminal amine group linked thereto are deleted;
   wherein the non-peptidyl polymer is selected from the group consisting of polyethylene glycol, polypropylene glycol, copolymers of ethylene glycol and propylene glycol, polyoxyethylated polyols, polyvinyl alcohol, polysaccharides, dextran, polyvinyl ethyl ether, biodegradable polymers, lipid polymers, chitins, hyaluronic acid, and combinations thereof; and
   wherein one end of the non-peptidyl polymer is linked to an amino acid residue other than the N-terminus of the insulinotropic peptide.

2. An insulinotropic peptide conjugate according to claim 1, wherein lysine at the 12$^{th}$ position of the extendin-4 is substituted with serine or arginine.

3. The insulinotropic peptide conjugate according to claim 1, wherein the non-peptidyl polymer has both ends, each binding to an amine group or a thiol group of the immunoglobulin Fc region, and the insulinotropic peptide.

4. The insulinotropic peptide conjugate according to claim 1, wherein the immunoglobulin Fc region is deglycosylated.

5. The insulinotropic peptide conjugate according to claim 1, wherein the immunoglobulin Fc region is composed of one to four domains selected from the group consisting of $C_H1$, $C_H2$, $C_H3$ and $C_H4$ domains.

6. The insulinotropic peptide conjugate according to claim 5, wherein the immunoglobulin Fc region further includes a hinge region.

7. The insulinotropic peptide conjugate according to claim 1, wherein the immunoglobulin Fc region is an Fc region derived from an immunoglobulin selected from the group consisting of IgG, IgA, IgD, IgE, and IgM.

8. The insulinotropic peptide conjugate according to claim 7, wherein each domain of the immunoglobulin Fc region is a domain hybrid of a different origin derived from an immunoglobulin selected from the group consisting of IgG, IgA, IgD, IgE, and IgM.

9. The insulinotropic peptide conjugate according to claim 7, wherein the immunoglobulin Fc region is a dimer or a multimer composed of single-chain immunoglobulins of the same origin.

10. The insulinotropic peptide conjugate according to claim 7, wherein the immunoglobulin Fc region is an IgG4 Fc region.

11. The insulinotropic peptide conjugate according to claim 10, wherein the immunoglobulin Fc region is a human deglycosylated IgG4 Fc region.

12. The insulinotropic peptide conjugate according to claim 1, the non-peptidyl polymer has a reactive group at one or both of its ends, said reactive group being selected from the group consisting of an aldehyde group, a propionaldehyde group, a butyraldehyde group, a maleimide group, and a succinimide derivative.

13. The insulinotropic peptide conjugate according to claim 12, wherein the succinimide derivative is selected from the group consisting of succinimidyl propionate, succinimidyl carboxymethyl, hydroxy succinimidyl, and succinimidyl carbonate.

14. The insulinotropic peptide conjugate according to claim 12, wherein the non-peptidyl polymer has a reactive aldehyde group at both ends.

15. The insulinotropic peptide conjugate according to claim 14, wherein the non-peptidyl polymer is polyethylene glycol.

16. An insulinotropic peptide conjugate according to claim 1, which is represented by the following Chemical Formula 1:

$$R_1—X—Y—Z—R_2 \quad <\text{Formula 1}>$$

wherein, $R_1$ is selected from the group consisting of N-dimethyl-histidyl group, beta-hydroxy imidazopropionyl group and 4-imidazoacetyl group;

$R_2$ is selected from the group consisting of —NH, —OH and -Lys;

X is a sequence selected from the group consisting of SEQ ID NO: 4, and SEQ ID NO: 5;

Y is polyethylene glycol, polypropylene glycol, copolymers of ethylene glycol and propylene glycol, polyoxyethylated polyols, polyvinyl alcohol, polysaccharides, dextran, polyvinyl ethyl ether, biodegradable polymers, lipid polymers, chitins, hyaluronic acid, and combinations thereof; and Z is an immunoglobulin Fc region.

17. A method for preparing the insulinotropic peptide conjugate according to claim 1, comprising the steps of:
(1) covalently linking a non-peptidyl polymer having a reactive group selected from the group consisting of aldehyde, maleimide, and succinimide derivatives at both ends thereof, with an amine or thiol group of an insulinotropic peptide;
(2) isolating a conjugate comprising the insulinotropic peptide from the reaction mixture of (1), in which the non-peptidyl polymer is linked covalently to an amino acid other than the amino acid at the N-terminus; and
(3) covalently linking an immunoglobulin Fc region to the other end of the non-peptidyl polymer of the isolated conjugate to produce the insulinotropic peptide conjugate comprising the immunoglobulin Fc region and the insulinotropic peptide, which are linked to each end of the non-peptide polymer, wherein the insulinotropic peptide is selected from the group consisting of beta-hydroxy-imidazo-propionyl exendin-4 where the N-terminal amine group of exendin-4 is substituted with hydroxyl group, dimethyl-histidyl exendin-4 where the N-terminal amine group of exendin-4 is modified with two methyl groups, and imidazo-acetyl exendin-4 where the alpha carbon of the first histidine and the N-terminal amine group linked thereto are deleted.

18. A method for preparing the insulinotropic peptide conjugate according to claim 1, comprising the steps of:
(1) covalently linking a non-peptidyl polymer having an aldehyde reactive group at both ends thereof with the lysine residue of the insulinotropic peptide at pH of 7.5 or more;
(2) isolating a conjugate comprising the insulinotropic peptide from the reaction mixture of (1), in which the non-peptidyl polymer is linked covalently to the lysine residue; and
(3) covalently linking an immunoglobulin Fc region to the other end of the non-peptidyl polymer of the isolated conjugate to produce a protein conjugate comprising the immunoglobulin Fc region and the insulinotropic peptide, which are linked to each end of the non-peptidyl polymer.

19. The method for preparing an insulinotropic peptide conjugate according to claim 17, wherein the exendin-4 is further substituted at lysine at the amino acid position 12 with serine or arginine.

20. The method for preparing an insulinotropic peptide conjugate according to claim 18, wherein the exendin-4 is further substituted at lysine at the amino acid position 12 with serine or arginine.

* * * * *

SEQUENCE LISTING

```
<160> NUMBER OF SEQ ID NOS: 5

<210> SEQ ID NO 1
<211> LENGTH: 31
<212> TYPE: PRT
<213> ORGANISM: Homo sapiens
<220> FEATURE:
<222> LOCATION: 1..31
<223> OTHER INFORMATION: GLP-1(7-37)

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 39
<212> TYPE: PRT
<213> ORGANISM: Heloderma suspectum
<220> FEATURE:
<222> LOCATION: 1..39
<223> OTHER INFORMATION: Exendin-3

<400> SEQUENCE: 2

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 3
<211> LENGTH: 39
<212> TYPE: PRT
<213> ORGANISM: Heloderma suspectum
<220> FEATURE:
<222> LOCATION: 1..39
<223> OTHER INFORMATION: Exendin-4

<400> SEQUENCE: 3

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 4
<211> LENGTH: 38
<212> TYPE: PRT
<213> ORGANISM: Artificial
<220> FEATURE:
<221> NAME/KEY: misc_feature
<222> LOCATION: 11..11
<223> OTHER INFORMATION: Lys, Ser, or Arg
```

```
<220> FEATURE:
<223> OTHER INFORMATION: Synthetic construct

<400> SEQUENCE: 4

Gly Glu Gly Thr Phe Thr Ser Asp Leu Ser Xaa Gln Met Glu Glu Glu
1               5                   10                  15

Ala Val Arg Leu Phe Ile Glu Trp Leu Lys Asn Gly Gly Pro Ser Ser
            20                  25                  30

Gly Ala Pro Pro Pro Ser
        35

<210> SEQ ID NO 5
<211> LENGTH: 29
<212> TYPE: PRT
<213> ORGANISM: Artificial
<220> FEATURE:
<221> NAME/KEY: misc_feature
<222> LOCATION: 11..11
<223> OTHER INFORMATION: Lys, Ser, or Arg
<220> FEATURE:
<223> OTHER INFORMATION: Synthetic construct

<400> SEQUENCE: 5

Gly Glu Gly Thr Phe Thr Ser Asp Leu Ser Xaa Gln Met Glu Glu Glu
1               5                   10                  15

Ala Val Arg Leu Phe Ile Glu Trp Leu Lys Asn Gly Gly
            20                  25
```